(12) United States Patent
Stern et al.

(10) Patent No.: US 11,268,960 B2
(45) Date of Patent: Mar. 8, 2022

(54) ASSAYS FOR IMPROVING AUTOMATED ANTIMICROBIAL SUSCEPTIBILITY TESTING ACCURACY

(71) Applicant: SELUX DIAGNOSTICS, INC., Charlestown, MA (US)

(72) Inventors: Eric Stern, Charlestown, MA (US); Kelly Flentie, Charlestown, MA (US); Nicholas Phelan, Charlestown, MA (US)

(73) Assignee: SELUX DIAGNOSTICS, INC., Charlestown, MA (US)

( * ) Notice: Subject to any disclaimer, the term of this patent is extended or adjusted under 35 U.S.C. 154(b) by 44 days.

(21) Appl. No.: 16/245,092

(22) Filed: Jan. 10, 2019

(65) Prior Publication Data
US 2019/0212339 A1     Jul. 11, 2019

Related U.S. Application Data

(60) Provisional application No. 62/615,732, filed on Jan. 10, 2018.

(51) Int. Cl.
| | |
|---|---|
| *G01N 33/573* | (2006.01) |
| *G01N 33/50* | (2006.01) |
| *G01N 33/58* | (2006.01) |
| *C12Q 1/04* | (2006.01) |
| *C12Q 1/34* | (2006.01) |

(52) U.S. Cl.
CPC ............ *G01N 33/573* (2013.01); *C12Q 1/04* (2013.01); *C12Q 1/34* (2013.01); *G01N 33/5008* (2013.01); *G01N 33/582* (2013.01); *C12Y 305/02006* (2013.01); *G01N 2333/986* (2013.01)

(58) Field of Classification Search
None
See application file for complete search history.

(56) References Cited

U.S. PATENT DOCUMENTS

| | | |
|---|---|---|
| 8,097,434 B2 | 1/2012 | Yang-Woytowitz et al. |
| 9,187,499 B2 | 11/2015 | Nagano et al. |
| 9,632,085 B2 | 4/2017 | Super et al. |
| 10,161,948 B2 | 12/2018 | Otten et al. |
| 2005/0095665 A1 | 5/2005 | Williams et al. |
| 2009/0023181 A1 | 1/2009 | Sei et al. |
| 2012/0077215 A1 | 3/2012 | Yang-Woytowitz et al. |
| 2014/0295417 A1 | 10/2014 | von Stein et al. |
| 2016/0281125 A1 | 9/2016 | Deck et al. |
| 2018/0305730 A1 | 10/2018 | Baunoch et al. |

FOREIGN PATENT DOCUMENTS

| | | | |
|---|---|---|---|
| WO | 2017089823 A1 | 6/2017 | |
| WO | 2017127727 A1 | 7/2017 | |
| WO | 2017218202 A1 | 12/2017 | |
| WO | WO-2017218202 A1 * | 12/2017 | ............. G01N 35/10 |
| WO | 2018111234 A1 | 6/2018 | |
| WO | 2018119439 A1 | 6/2018 | |
| WO | 2018144918 A1 | 8/2018 | |

OTHER PUBLICATIONS

Daly, Jennifer S; et al; "Effect of Zinc Concentration in Mueller-Hinton Agar on Susceptibility of Pseudomonas aeruginosa to Imipenem" Journal of Clinical Microbiology, 35, 1027-1029, 1997 (Year: 1997).*
Jorgensen, James H; Lee, Jean C; "Microdilution Technique for Antimicrobial Susceptibility Testing of Haemophilus influenzae" Antimicrobial Agents and Chemotherapy, 8, 610-611, 1975 (Year: 1975).*
International Search Report and Written Opinion for International application No. PCT/US2019/013100, dated Jul. 1, 2019, 17 pages.
Castanheira, M., et al., "Antimicrobial Activities of Tigecycline and Other Broad-Spectrum Antimicrobials Tested against Serine Carbapenemase- and Metallo-beta-Lactamase-Producing Enterobacteriaceae: Report from the SENTRY Antimicrobial Surveillance Program", Antimicrobial Agents and Chemotherapy, 52(2):570-573 (2008).
International Search Report and Written Opinion for International application No. PCT/US2020/041547, dated Nov. 20, 2020, 12 pages.
Supplementary European Search Report for Application No. EP19738711.1, dated Oct. 6, 2021, 15 pages.

* cited by examiner

*Primary Examiner* — David W Berke-Schlessel
(74) *Attorney, Agent, or Firm* — Kacvinsky Daisak Bluni PLLC

(57) ABSTRACT

Phenotypic antimicrobial susceptibility testing (AST), the gold-standard diagnostic that indicates whether an antimicrobial will be clinically effective, often suffer the slowest times-to-result for the most resistant pathogens. Here we introduce novel assays to be performed in parallel with standard AST assays that enable rapid, same-shift reporting of AST results for a plurality of pathogens. The assays developed here are further capable of detecting resistance to carbapenems, the most powerful class of beta-lactams commonly used as "last-resort" antimicrobials.

24 Claims, 1 Drawing Sheet

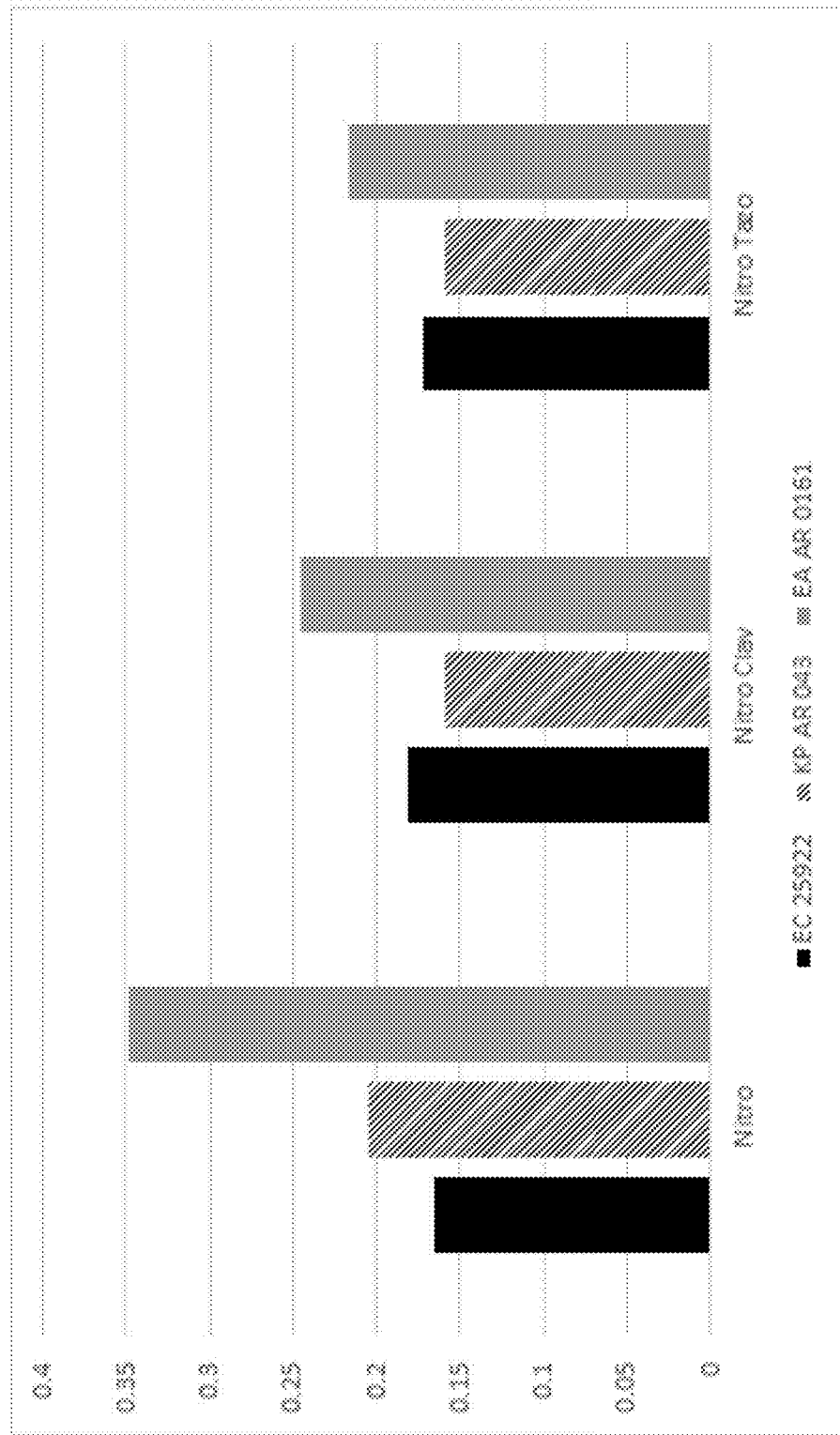

ASSAYS FOR IMPROVING AUTOMATED ANTIMICROBIAL SUSCEPTIBILITY TESTING ACCURACY

CROSS-REFERENCE TO RELATED APPLICATIONS

This application claims the benefit of priority under 35 U.S.C., § 119 to U.S. Provisional Patent Application No. 62/615,732 by Eric Stern et al., filed on Jan. 10, 2018, which is incorporated by reference herein in its entirety and for all purposes.

FIELD OF THE DISCLOSURE

This disclosure relates generally to antimicrobial susceptibility testing, and more specifically to performing automated rapid antimicrobial susceptibility testing and antimicrobial resistance testing.

BACKGROUND

Beta-lactam antibiotics are widely prescribed, accounting for ~70% of US antimicrobial prescriptions. These drugs act on the enzymes responsible for microbial cell wall synthesis, degradation, and reassembly, which have no close analogs in eukaryotic cells. However, their use has triggered microbes to gain resistance, commonly through enzymes known as beta-lactamases, which specifically degrade beta-lactams. In order to combat such resistance, carbapenems, the broadest, most effective class of beta-lactams were developed, including imipenem, ertapenem, doripenem, and meropenem. But beta-lactamase enzymes capable of degrading carbapenems, termed carbapenemases, are now increasing in frequency. Another method developed for extending beta-lactam efficacy are combination therapies that include the beta-lactam drug together with a small molecule inhibitor that binds the beta-lactamase enzyme, often covalently, and terminates its degradation ability.

Current FDA-approved combination beta-lactam/beta-lactamase inhibitor therapies include ampicillin-sulbactam, amoxicillin-clavulanate, piperacillin-tazobactam, ceftazidime-avibactam, meropenem-vaborbactam, and ceftolozane-tazobactam. Among these, Avibactam and vaborbactam are new beta-lactamase inhibitors capable of inhibiting broader classes of beta-lactams than previous generations. Additional combination therapies are in development, including by Spero Therapeutics, Pfizer, and Merck.

Phenotypic AST is the gold-standard method for determining clinical efficacy of antibiotics. The key test output is the minimum inhibitory concentration (MIC). The MIC is determined for each antimicrobial by testing the growth of a microbe sample in multiple antimicrobial dilutions in parallel and determining the lowest antimicrobial concentration that effectively inhibited microbial growth. As dictated by the Centers for Laboratory Standards Institute (CLSI) M100 reference manual for broth microdilution (BMD) AST, doubling (serial) dilutions of antibiotics are the standard.

Uniquely for some combination beta-lactam/beta-lactamase inhibitor agents, doubling dilutions are not prescribed by the CLSI. For example, for piperacillin-tazobactam, piperacillin (the beta-lactam antibiotic) follows standard doubling dilutions while tazobactam (the beta-lactamase inhibitor) remains at a constant concentration across all piperacillin concentrations. Similar constant-inhibitor concentrations are prescribed by the CLSI for the three recently-approved drugs, ceftazidime-avibactam, meropenem-vaborbactam, and ceftolozane-tazobactam.

Because inhibitor concentrations are held constant, these assays may be susceptible to confounding errors relating to the differential induction of lactamase enzymes at different beta-lactam concentrations. These potential errors may be further compounded by rapid AST platforms that deliver "same-shift" results, e.g. in under 6 hours.

The desire to have same-shift results may also compromise the accuracy of MIC determinations for carbapenems. This may be caused by the phenomenon of heteroresistance in carbapenemase-producing strains. Such strains express resistant phenotypes as only a fraction of their cells, generally 1 in $10^5$-$10^6$ cells. Thus, rapid assays may be prone to false susceptibility calls.

Multiple tests for beta-lactamase detection have been developed, as is well known to those skilled in the art. These include chromogenic probes, such as nitrocefin, PADAC, and GENTA, which produce a color upon beta-lactamase degradation. Fluorescent probes that operate on similar principles and improve beta-lactamase sensitivities have also been developed by multiple research groups. Additional tests include iodometric and acidimetric tests, which take advantage of the chemistries of the products of beta-lactam degradation by beta-lactamases. Acidimetric tests, in particular, provide the basis of current carbapenemase tests. Additional assays include those present on automated platforms that test for the presence of "extended-spectrum beta-lactamases" (ESBLs) using three cephalosporin agents, each with and without clavulanate.

Chromogenic probes are often used for routine resistance testing for *Maemophilus, Moraxella*, and *Neisseria* spp., because beta-lactamase presence in these species is rare. However, such non-specific beta-lactamase probes are not routinely used in Enterobacteriaceae, *Psuedomonas aeruginosa*, and *Acinetobacter baumannii* because these species often express multiple beta-lactamases.

SUMMARY

The present disclosure provides systems and methods that improve the accuracy of AST results for combination beta-lactam/beta-lactamase inhibitors and limit the potential for confounding errors described above. These systems and methods reconcile the different conditions under which AST assays and carbapenemase or beta-lactamase assays are currently conducted, allowing the integration of both assays into a single testing process that can be performed by an automated AST platform.

In one aspect, the disclosure relates to a test assay performed with an assay cartridge containing a series of a beta-lactam antimicrobial, a series containing a beta-lactamase probe, and a series containing a beta-lactamase probe and a beta-lactamase inhibitor, where all the wells contain microbes. The series containing only the beta-lactam antimicrobial is a dilution series, and the remaining series are part of the beta-lactamase inhibitor assay. When used in an automated AST platform, it produces a report describing both the dilution series and the inhibitor assay.

In another aspect, the disclosure relates to a test assay performed with an assay cartridge containing a series of a carbapenem antimicrobial, a series containing a beta-lactamase probe, and a series containing a beta-lactamase probe and a beta-lactamase inhibitor, where all the wells contain microbes. The series containing only the carbapenem antimicrobial is a dilution series, and the remaining series are part of the carbapenem assay. When used in an automated AST platform, it produces a report describing both the dilution series and the carbapenem assay.

In other embodiments, the disclosure relates to a test assay performed with an assay cartridge containing a dilution series of a carbapenem antimicrobial and an assay specific for determining carbapenemase activity. Each well of the carbapenemase assay contains at least one of the following: saline, the carbapenem, an ionic zinc, microbes, and a pH indicator. When used in an automated AST platform, the results from the carbapenemase assay may be used as an input to algorithm that determines the minimum inhibitory concentration (MIC) of the carbapenem dilution series that is reported to the user. In particular, if the carbapenemase assay determines the presence of a carbapenemase enzyme, this information may drive a change in algorithmic interpretation such that carbapenem MICs are interpreted to be higher (more resistant) than they might be in the absence of a positive result in the carbapenemase assay. The effect the carbapenemase assay data has on the algorithmic interpretations of different carbapenems may be different, i.e. the effect a positive carbapenemase assay result has on an imipenem MIC may be different from that it has on a meropenem or an ertapenem MIC. The results from the carbapenemase assay may also be used to report carbapenemase presence to the user.

In an exemplary embodiment, the carbapenemase assay is performed with intact microbes and comprises a minimum of 4 wells. The first well ($Well_1$) comprises saline, a carbapenem, ionic zinc, and a pH indicator. The second well comprises saline, a carbapenem, ionic zinc, a pH indicator, and a microbe sample comprising $<1\times10^8$ CFU microbes. The third well comprises saline, ionic zinc, and a pH indicator. The fourth well comprises saline, ionic zinc, a pH indicator, and a microbe sample comprising $<1\times10^8$ CFU microbes. The following formula can then be utilized to normalize the result:

$$\text{Normalized Activity} = (Well_1 - Well_2) - (Well_3 - Well_4) \quad [\text{Formula 1}]$$

The above says that imipenem degradation is the change in pH (e.g. loss of signal) due to the presence of microbes less the change in pH (e.g. loss of signal) due to microbes in solution only.

In additional embodiments, acidimetric methods may be utilized for testing inhibitors. For example, the addition of an inhibitor with known carbapenemase activity, such as avibactam or vaborbactam, to an additional well of the carbapenemase assay described above may serve as an assay for inhibitor activity.

The assays described above may be performed in a cell culture plate. The cell culture plate may comprise 48, 96, or 384 wells. The assay may be performed using 4 wells.

The assays described in this disclosure may comprise an automated antimicrobial susceptibility test (AST) assay. This assay may comprise an assay cartridge comprising an AST testing panel, a beta-lactamase testing panel comprising a plurality of assay wells where the assay wells comprise a beta-lactam and a microbial inoculum, and a beta-lactamase inhibitor assay comprising at least one assay well wherein the assay well comprises a beta-lactamase probe and a microbial inoculum, and a plurality of assay wells, wherein the assay wells comprise a beta-lactamase inhibitor, and a microbial inoculum. The AST testing panel may further comprise a plurality of test wells defining a plurality of dilution series for at least 10, 11, 12, 13, 14, 15, 16, 17, or 18 antimicrobial agents. The assay may be performed using an automated AST platform and the automated AST platform may produce a report comprising information describing the beta-lactam assay and the beta-lactamase inhibitor assay. The concentration of microbial inoculum may be similar in all test wells. The beta-lactamase probe may be capable of observing beta-lactamase degradation.

The assays of this disclosure may be performed using a carbapenem. The carbapenem may have a concentration between 0-3 mg/mL. The carbapenem may include, but is not limited to, imipenem, ertapenem, doripenem, and meropenem.

The assays of this disclosure may be performed using a beta-lactam antimicrobial. The beta-lactam may have a concentration of 0-300 μg/mL. The beta-lactam antimicrobial may include cefotaxime, ampicillin, amoxicillin, piperacillin, ceftazidime, and ceftolozane.

The assays of this disclosure may be performed using a beta-lactamase inhibitor. The beta-lactamase inhibitor may have a concentration of 0-500 μg/mL. The beta-lactamase inhibitor may include clavulanate, cloxacillin, tazobactam, avibactam, vaborbactam, and relebactam.

In this disclosure, the assays may have an amount of antimicrobial of around 15 μg, a concentration of pH indicator of around 5-10 μM, a volume of saline around 100 μL and a concentration of ionic zinc of around 0.05 mM. The total volume of the well may be 0-200 μL.

The assays of the current disclosure may be performed in sequence with AST tests. When used in sequence with growth check and AST tests, as described in greater detail in PCT/US2017/068306, published as WO2018/119439 with specific reference to paragraphs [0366-0370] and FIGS. 4B-7, which are incorporated by reference herein, the assays are performed at the growth check stage.

The antimicrobial and other carbapenemase assay components may be pre-loaded on the well plate. Further, the antimicrobial and other carbapenemase assay components may be dried into a powder.

The foregoing listing is intended to be exemplary rather than limiting, and skilled artisans will appreciate additional aspects of the disclosure, as well as modifications to the aspects and embodiments described above.

In some embodiments, an incubator chamber can be included to maintain an optimal growth temperature for the organism under test. Unlike other conventional systems, in some examples, the systems and methods herein can include an incubator that provides or otherwise allows agitation of test panels. In some cases, orbital shaking can improve oxygenation and can allow continuous and more uniform exposure of microorganisms to nutrients in growth medium. Agitation can further increase the uniformity of microorganism exposure to antimicrobial compounds. These may, in some cases, increase growth and shorten time needed to quantify MIC and/or QSR.

In some embodiments, the systems herein can include an optical system that can include an optical excitation source (e.g., xenon lamp, light emitting diode (LED)), a set of optical filters (e.g., discrete filters, monochromators) with desired characteristics (e.g., band-pass, band-stop, central wavelength, full width half max (FWHM)), and an optical detector (e.g., photomultiplier tube). The optical systems can also include data acquisition and processing electronics used to collect and process data. In some cases, the optical system can include one or more components, such as fiber optics and collection optics, nested in, or otherwise disposed within or on, a robotic arm used to move cartridges throughout the system. Such a configuration can help achieve a faster sample processing and time for results readout. These optics can carry a signal from cartridges to the detector and data processing electronics.

In yet another aspect, a liquid handling system can be included and used to deliver and/or remove (e.g., aspirate) reagents to and from the test wells within the cartridges.

In another aspect, a separation method can be included, which can be used to remove excess fluid from test wells that could interfere with the various assays performed. This step can be a part of the washing process step and can include one or more of various procedures, such as centrifugation, magnetic separation, or vacuum filtration. For example, in some embodiments, centrifugation separation can be used to separate (e.g., pellet) microorganisms. In some cases, the separation can be followed by an aspiration process step to remove supernatant fluid. In some embodiments, the term wash sequence can refer to a centrifugation, aspiration, and liquid buffer additional (e.g., assay or wash buffer).

In some aspects, automated rapid antimicrobial susceptibility testing systems for performing a multi-assay testing sequence can include: an automated incubation assembly comprising a nest assembly adapted to house at least one test panel (e.g., cartridge) having a plurality of wells for receiving a sample comprising microorganisms originating from a clinical sample, the incubation assembly facilitating incubation of one or more test panels in order to undergo the multi-assay testing sequence; a robotic handling assembly configured to accept one or more incoming test panels and move them to and from the incubation assembly for incubation between each assay of the multi-assay testing sequence; an automated liquid handling assembly configured to exchange one or more fluids in the plurality of wells of the test panels; and an optical assembly for interrogation and readout of each assay of the multi-assay testing sequence being performed in the plurality of wells.

Embodiments can include one or more of the following features.

In some embodiments, the systems can include a sample separation assembly configured to separate microorganisms from a remainder of the sample within the wells of test panel. For example, the sample separation assembly can form a pellet of the microorganisms within the wells of the test panels. The separation assembly can be a centrifugation system. The separation assembly can include a magnetic capture separation system. The separation assembly can include a vacuum filtration system.

The incubation assembly can be configured to agitate the test panel during incubation. The incubation assembly can include a drive system to agitate the nest assembly carrying the at least one test panel. The drive system can be configured to impart an orbital speed on the nest assembly that is variable. The speed can be between 100 and 650 RPM. A radius of an agitation orbit can be adjustable. A radius of an agitation orbit can be about 1 mm to about 10 mm.

The optical assembly can be mounted on or integrally formed within a robotic arm of the robotic handling assembly. The optical assembly can be configured to measure at least one of absorbance, fluorescence, luminescence, time-resolved fluorescence, or time-gated luminescence emitted from the sample during the multi-assay testing sequence. An excitation wavelength to generate a fluorescence emission can be about 560 nm and a wavelength of the emission can be about 590 nm. An excitation wavelength to generate a time-gated luminescence emission can be from about 280 nm to about 360 nm and a wavelength of the emission can be about 608 nm to about 623 nm. The optical assembly can include two or more optical filters for interrogation and readout of each assay of the multi-assay testing sequence being performed in the plurality of wells. Two optical filters can be disposed on an indexing component configured to selectively position a first optical filter in line with an excitation source and a second optical filter in line with an optical detector. The indexing component can include a second set of two filters, and where an indexing motion of the indexing component replaces the optical filter in-line with the excitation source and the optical filter in-line with the optical detector.

The fluid handling assembly can include a liquid addition system and an aspiration system. Reagents can be stored in a disposable container. The container can be disposed of and replaced after at least every shift, at least every 1 day, at least every 5 days, or at least every week. The container can be disposed of and replaced after at least every testing sequence, every 10 testing sequences, every 20 testing sequences, every 50 testing sequences, or every 100 testing sequences.

The system can be configured to process simultaneously at least 2, at least 4, at least 6, at least 8, at least 10, or at least 12 test panels. The system can be configured to yield a testing sequence throughput of at least 2, at least 4, at least 6, at least 8, at least 10, at least 12, at least 16, at least 20 test panels per hour. A time duration for processing a test panel through the testing sequence from insertion of the test panel into the system to obtaining a result can be less than 8 hours, less than 6 hours, less than 5 hours, less than 4 hours, less than 3 hours, or less than 2 hours.

In some aspects, methods for performing multi-assay rapid antimicrobial susceptibility testing sequences can include: inoculating a sample comprising a microorganism derived from a clinical sample into a plurality of wells of a test panel (e.g., a cartridge), at least a portion of the plurality of wells containing one or more antimicrobials of a plurality of antimicrobials for inoculation of the sample; loading the test panel into an automated rapid antimicrobial susceptibility testing system for performing a multi-assay testing sequence; and operating the testing system to: move the loaded test panel to an incubation assembly; incubate and agitate the inoculated sample in the incubation assembly; at least once, periodically measure an amount of sample growth in a plurality of control wells of the plurality of wells; responsive to determining that a level of growth in the control wells meets or exceeds a threshold level of growth, stop incubation; perform one or more end point assays on incubated samples in the test panel; measure an optical output from the sample in the plurality of wells of the test panel, the optical output corresponding to an amount of the microorganism remaining in each of the plurality of wells; and report at least one of: a minimum inhibitory concentration of and/or a qualitative susceptibility interpretation for the microorganism remaining in each of the plurality of wells and the plurality of antimicrobials.

Embodiments can include one or more of the following features.

The performing the end point assay can include one or more of: liquid handling, centrifugation, incubation, or shaking of the sample. The liquid handling can include performing one or more aspiration liquid addition steps.

The performing the end point assay can include a plurality of binding steps. An amplification species of the binding steps can include a catalyst. An amplification species of the binding steps can include a europium chelate.

The methods and testing systems can be configured to process simultaneously at least 2, at least 4, at least 6, at least 8, at least 10, or at least 12 test panels. The methods and testing systems can be configured to yield a testing sequence throughput of at least 2, at least 4, at least 6, at least 8, at least 10, at least 12, at least 16, at least 20 test panels per hour. A time duration for processing a test panel through the testing sequence from insertion of the test panel into the testing system to obtaining a result using the methods can be less than 8 hours, less than 6 hours, less than 5 hours, less than 4 hours, less than 3 hours, or less than 2 hours.

In some aspects antimicrobial susceptibility testing system sample cartridge handling devices can include: a robotic gripping portion having an interface configured to be coupled by a gripping mechanism of a robotic arm; and a set of lifting fingers sized and configured to support a sample cartridge, the lifting fingers defining a cartridge platform.

Embodiments can include one or more of the following features.

The set of fingers can include one or more cartridge positioning features that define the cartridge platform and limit the cartridge from sliding relative to the fingers. The cartridge positioning features can include vertical ridges. The fingers can be laterally separated by at least about 3 inches. A distal end of at least one of the fingers can be tapered.

The interface of the robotic gripping portion can include a set of protrusions extending laterally to couple to the gripping mechanism of the robotic arm. A distal end of the gripping portion can be adjustable in width from at least about 3 inches to about 4 inches. The gripping mechanism can be operated at least in part by a linear actuator and linkage to articulate one or more gripping arms. The gripping mechanism can be operated at least in part by a linear spring mechanism in connection with linkage to articulate one or more gripping arms.

In some aspects, incubation systems for a sample testing system can include: a tiered frame configured comprising one or more floors, each floor comprising: a stage to accommodate a sample testing cartridge; one or more cartridge positioning features extending from the stage; and a set of recesses to accommodate a test cartridge handling device; and an agitation system configured to generate a repeated motion of the tiered frame.

Embodiments can include one or more of the following features.

The tiered frame can include multiple floors where each floor comprises two surfaces to accommodate two sample testing cartridges. The one or more cartridge positioning features can include a vertical ridge along a front or rear end of the stage to accommodate a testing cartridge. The floor can include a heating element disposed in or along the stage.

The agitation system can be configured to axially or orbitally agitate the frame. The agitation system can include a rotational agitation system having a rotating oscillating component. The agitation system can include a bearing surface along which the rotating oscillating component interfaces during rotation. The bearing surface can include a roller bearing. The rotating oscillating component can include a counter balance weight. The agitation system can include one or more linear actuators. The agitation system can include one or more linear bearing surfaces. The agitation system can include two linear bearing surfaces positioned substantially perpendicularly with respect to one another. The agitation system can include two linear bearing rails and sliding stages configured to slide along the bearing rails.

The agitation system can be configured to agitate the frame along an orbital path having a radius that is less than about 25 mm. The agitation system can be configured to agitate the frame along an orbital path having a radius that is from about 1 mm to about 12 mm. The agitation system can be configured to vary a radius of the orbital path of agitation. The agitation system can be configured to agitate the frame along an orbital path at a rate of greater than about 75 revolutions per minute. The agitation system can be configured to agitate the frame along an orbital path at a rate of about 150 revolutions per minute to about 650 revolutions per minute. The agitation system can be configured to vary the rate at which the frame travels along the orbital path of agitation.

The incubation system can include a cover along a front face of the frame. The frame can define a front opening along a front face and a rear opening along a rear face. The frame can be configured to receive a cartridge from a user through the front opening and the cartridge can be removed by a handling device of an automated system through the rear opening.

In some aspects, methods of aspirating fluid from one or more chambers in a cartridge can include: displacing one or more microorganisms suspended in the fluid within the chambers using a centrifugal force; and aspirating a first fluid from a first chamber from a location substantially opposite the displaced microorganisms with respect to a central region of the first chamber.

Embodiments can include one or more of the following features.

The displacing one or more microorganisms suspended in the fluid can include running the cartridge through a centrifugation system. The aspirating the first fluid from the first chamber can include disposing an aspiration nozzle of a fluid processing system coupled to robotic arm into the first chamber.

The methods can include aspirating a second fluid from a second chamber from a location substantially opposite a second set of displaced microorganisms with respect to a central region of the second chamber. The aspirating the second fluid from the second chamber can occur at a location within the second chamber that is different than the location at which the first fluid is aspirated from the first chamber within the respective central regions of the first and second chambers. The aspirating the second fluid from the second chamber can occur at a location within the second chamber that is substantially opposite the location at which the first fluid is aspirated from the first chamber with respect to a central region of the cartridge.

Various aspects of the systems and methods described herein can have one or more of the following advantages.

In some aspects, the systems and methods herein provide for rapid AST and determination of MICs for antimicrobial panels. These MICs, along with the microorganism species and antimicrobial, are used to determine the Clinical & Laboratory Standards Institute (CLSI) breakpoint interpretation to provide the clinical AST result for each combination of microorganism species and antimicrobial. Such results take the form of Susceptible (S), Intermediate (I) or Resistant (R) per CLSI publication M-100S. For certain antimicrobials, Not Susceptible (NS), and No Interpretation (NI) may be used.

According to CLSI Microbiology standards, an MIC of a given antimicrobial for a given species and strain of a microorganism is defined as the lowest concentration of the antimicrobial in two-fold dilution series that inhibits growth of the microorganism. According to the CLSI manuals and the FDA guidance document for Automated AST systems, a typically preferred standard for this procedure is performed manually, after 16-20 hours of incubation of a 96 well round bottom microwell plate cartridge, and after inoculation with a sample in Muller-Hinton broth. Cartridges meeting standard microplate dimension requirements can be advantageous for handling. The reading can be done manually (e.g., by eye) by a skilled technician. This procedure is very cumbersome, often expensive, and typically requires a lot of hands on technician time and operational planning. Several automated systems have been introduced over the past 30 years. Many automated systems speed the determination of microorganism growth through the use of optical probes. Though these systems may speed growth determination, they are often not capable of providing accurate AST results within the 5-hour "same-shift" cutoff desired or required by microbiology laboratories. In such systems, an algorithm determines the MIC after a sufficient amount of information is collected (e.g., relating to growth amount, rate, etc.) such that the algorithm may decide the MIC with a high confidence level. Because of this, results are not reported at a deterministic (e.g., a pre-defined) time but rather scattered throughout a 24-hour period. Inability to deliver AST results on a consistent schedule and within the same work shift (e.g., for a doctor or a nurse), often delays the delivery of targeted antimicrobial therapies, slows recovery and may, in some cases, increase mortality.

The systems and methods described herein address and reduce some of the drawbacks discussed above with respect to prior systems by separating the process into two or more steps. For example, first, a preliminary testing sequence (e.g., a checkpoint assay) is run for a period of time (e.g., 2-4 hours) after incubation starts. If growth measured during the checkpoint assay is found to be sufficient, the system can start the analysis sequence (e.g., the end point assays (e.g., the final growth/viability assays (e.g., an amplification assay))). If growth measured during the checkpoint assay is not found to be sufficient, the system can incubate for an additional time period (e.g., 8 hours) since slow growing organism are detected (i.e., due to the lack of sufficient growth per the checkpoint assay) and could utilize the additional growth time before the end point assay is performed. Such slow growing organisms are expected to account for less than 5% of all cases tested. Alternatively, the systems can be programmed to interrogate growth in control wells periodically until sufficient growth is achieved for initiation of the end point assay.

The current disclosure describes, in one embodiment, an automated antimicrobial susceptibility test assay which may comprise an assay cartridge which may have a plurality of assay wells. Within those assay wells may be a set of wells which contain a beta-lactam antimicrobial and a microbial inoculum. Another set of wells may contain a beta-lactamase inhibitor assay. The beta-lactamase inhibitor assay may contain at least one well with a beta-lactamase probe and a microbial inoculum and a plurality of wells with a beta-lactamase probe, a beta lactamase inhibitor, and a microbial inoculum.

The assay wells which contain a beta-lactam antimicrobial and a microbial inoculum may be an antimicrobial dilution series.

The antimicrobial susceptibility test assay may be performed using an automated AST platform. This automated AST platform may produce a report that gives information describing the beta-lactam assay and the beta-lactamase probe assay.

The beta-lactamase inhibitor assay may include a concentration of inhibitor between 0-300 µg/mL.

The automated antimicrobial susceptibility test assay may comprise a similar concentration of microbial inoculum in each test well.

The beta-lactamase probe of this disclosure may be capable of observing beta-lactamase degradation. Further, this probe may be chromogenic or fluorometric.

The beta-lactamase inhibitor of this disclosure may be one of clavulanate, cloxacillin, tazobactam, avibactam, and vaborbactam. This inhibitor may also be in a series of dilutions.

The microbial inoculum of this disclosure may be grown in the presence of one or more antimicrobials prior to the assay.

The beta-lactam and microbial inoculation assay of this disclosure may also comprise a beta-lactamase inhibitor.

The automated antimicrobial susceptibility test assay of this disclosure may further contain a plurality of beta-lactamase inhibitors.

In another embodiment, the automated antimicrobial susceptibility test assay may comprise an assay cartridge with a plurality of wells. In one set of these wells, a plurality of wells contain a carbapenem antimicrobial and a microbial inoculum. In a second set of these wells, a plurality of wells contain a carbapenemase assay wherein a set of wells contain a beta-lactamase probe and a microbial inoculum, and another set of wells contain a beta-lactamase probe, a microbial inoculum, and at least one inhibitor. In the wells containing a carbapenem and a microbial inoculum, these wells may comprise an antimicrobial dilution series. In the wells containing an inhibitor, the inhibitor may comprise clavulanate, cloxacillin, or tazobactam. The automated antimicrobial susceptibility test assay may be performed on an automated AST platform and may produce a report containing information describing the antimicrobial assay and the carbapenemase assay.

In another embodiment of the disclosure, an automated antimicrobial susceptibility test assay may comprise an assay cartridge. This assay cartridge may comprise a plurality of wells, one set of which contain a carbapenem and a microbial inoculum, and another set of which contain a carbapenem assay. The carbapenem assay may comprise one or more of the following in each well: saline, a carbapenem, an ionic zinc, a microbial inoculum, and a pH indicator. The carbapenem may be selected from imipenem and biapenem. The pH indicator may be fluorescein. The ionic zinc may be selected from zinc sulfate and zinc chloride. The microbial inoculum may comprise $<1\times10^8$ CFU intact microbes. The automated antimicrobial susceptibility test assay may be performed on an automated AST platform. The automated AST platform may produce a report describing the antimicrobial assay and the carbapenemase assay.

In some embodiments, the assay wells may be optically ready after 3.5 hours of incubation under conditions which promote microbial growth.

In other embodiments, additional wells may be used. These additional wells may comprise beta-lactamase inhibitors.

This disclosure further describes an embodiment wherein an automated antimicrobial susceptibility test assay for beta-lactam/beta-lactamase inhibitor antimicrobials. These assays consist of two or more assay wells comprising an antimicrobial dilution series for the specific beta-lactam antimicrobial inoculated at concentration $C_0$ and a beta-lactamase inhibitor assay probe inoculated at a concentration $C_R$ comprising one or more assay wells comprising a beta-lactamase and two or more assay wells comprising the same beta-lactamase probe and the specific beta-lactamase inhibitor at one or more concentrations. In this embodiment, all assays are run on a single cartridge and prepared from the same microbial inoculum and the final report from the automated AST platform comprises information from both the antimicrobial dilution assay and the inhibitor assay.

In this embodiment, the inhibitor assay may comprise one or more probes capable of beta-lactamase degradation present in all test wells, a similar concentration of microbes in all test wells, and a different concentration of inhibitor, which may be zero concentration, in one or more test wells. In this embodiment, the probe may be chromogenic or fluorometric. The probe may further be nitrocefin. The inhibitor may be one of clavulanate, cloaxacillin, tazobactam, avibactam, relebactam, and vaborbactam. The inhibitor assay may utilize multiple inhibitor dilutions. The sample may be grown in the presence of one or more antimicrobials prior to the onset of the inhibitor assay. The antimicrobial dilution assay may comprise the inhibitor. The inhibitor assay may comprise multiple beta-lactamase inhibitors.

In another embodiment, automated antimicrobial susceptibility test assays for one or more carbapenems may comprise two or more assay wells comprising an antimicrobial dilution series for the specific carbapenem antimicrobial, and a carbapenem assay comprising one or more assay wells comprising a beta-lactamase probe and two or more assays wells comprising the same beta-lactamase probe and two or more inhibitors selected from the list of clavulanate, cloxacillin, and tazobactam. In this embodiment, all assays are run on a single cartridge and prepared from the same microbial inoculum and the results of the carbapenemase assay influence algorithmic MIC determination of one or more carbapenems.

In another embodiment, automated antimicrobial susceptibility test assays for one or more carbapenems and/or beta-lactam/beta-lactamase inhibitors comprise two or more assay wells comprising an antimicrobial dilution series for the specific carbapenem antimicrobial, and a carbapenem assay comprising: one or more assay wells comprising saline, a carbapenem, ionic zinc, and a pH indicator; one or more assay wells comprising nutrient broth, a carbapenem, ionic zinc, a pH indicator, and a microbe sample comprising $<1\times10^8$ CFU intact microbes; one or more assay wells comprising saline, ionic zinc, and a pH indicator; and one or more assay wells comprising saline, ionic zinc, a pH indicator, and a microbe sample comprising $<1\times10^8$ CFU intact microbes. In this embodiment, all assays are run on a single cartridge and prepared from the same microbial inoculum and the results of the carbapenemase assay influence algorithmic MIC determinations of one or more carbapenems.

This embodiment may further include, but is not restricted to, a carbapenem selected from imipenem and biapenem. The pH probe may be any dye or fluorescent probe known to those skilled in the art to have its absorbance and/or emission properties change in response to solution pH, including but not limited to the following and their derivatives: fluorescein, rhodamine, pyranine, tinopal, cresol red, cresolphthalein, cresol purple, bromocresol green, dichlorofluorescein, methyl red, bromocresol green, bromocresol purple, chlorophenol red, bromothymol blue, phenol red, naphtholphthalein, phenolphthalein, cresolphthalein, thymolthalein, 2',7'-Bis(3-carboxypropyl)-5(6)-carboxyfluorescein, 8-Hydroxypyrene-1,3,6-trisulfonic acid trisodium salt, eosin, eosin diacetate, 7-hydroxycoumarin-3-carboxylic acid, 2-naphthol, 8-hydroxypyrene-1,3,5-trisulfonic acid trisodium salt. The ionic zinc may be selected from, but not limited to, zinc sulfate, zinc hydroxide, zinc chloride. The assay wells may be optically read after 2-10 hours, preferably within 7 hours, most preferably within 4 hours of incubation under conditions that promote microbial growth.

One or more additional wells may comprise beta-lactamase inhibitors. Additionally, in all cases zinc ions may be added to wells to promote the activity of specific metal-comprising beta-lactamases.

In another embodiment, a method for automated antimicrobial susceptibility testing comprises two or more assays described in other embodiments.

In yet another embodiment, a method of performing multi-assay rapid antimicrobial susceptibility testing sequences comprises inoculating two or more different concentrations of a sample comprising a microorganism derived from a clinical sample into a plurality of wells of a test panel, at least a portion of the plurality of wells containing one or more antimicrobials of a plurality of antimicrobials for inoculation of the sample, loading the test panel into an automated rapid antimicrobial susceptibility testing system for performing a multi-assay testing sequence, and operating the testing system is described. Operating the testing system may comprise moving the loaded test panel to an incubation assembly comprising a nest assembly adapted to: i) house at least one test panel, and ii) facilitate incubation of one or more test panels in order to undergo the multi-assay testing sequence the incubation assembly comprising an agitation system configured to generate a repeated motion of the nest assembly, incubating and agitating the inoculated sample in the incubation assembly, periodically measuring an amount of sample growth in a plurality of control wells of the plurality of wells, stop incubation if necessary, responsive to determining that a level of growth in the control wells meets or exceeds a threshold level of growth, perform an automated antimicrobial susceptibility test assays for one or more carbapenems and/or beta-lactam/beta-lactamase inhibitors on incubated samples in the test panel, perform one or more endpoint assays on incubated samples in the test panel, measure an optical output from the sample in the plurality of wells of the test panel, the optical output corresponding to an amount of the microorganism remaining in each of the plurality of wells; and report at least one of: a minimum inhibitory concentration and/or a qualitative susceptibility interpretation for the microorganism remaining in each of the plurality of wells and the plurality of antimicrobials, such that the results of the carbapenemase and/or beta-lactamase assays influence algorithmic MIC determinations of one or more carbapenems and/or beta-lactams.

Another aspect of the present disclosure describes a method of performing multi-assay rapid antimicrobial susceptibility testing sequences comprising two or more different concentrations of a sample comprising a microorganism derived from a clinical sample into a plurality of wells of a test panel, at least a portion of the plurality of wells containing one or more antimicrobials of a plurality of antimicrobials for inoculation of the sample, loading the test panel into an automated rapid antimicrobial susceptibility testing system for performing a multi-assay testing sequence, and operating the testing system is described. Operating the testing system may comprise moving the loaded test panel to an incubation assembly comprising a nest assembly adapted to: i) house at least one test panel, and ii) facilitate incubation of one or more test panels in order to undergo the multi-assay testing sequence the incubation assembly comprising an agitation system configured to generate a repeated motion of the nest assembly, incubating and agitating the inoculated sample in the incubation assembly, periodically measuring an amount of sample growth in a plurality of control wells of the plurality of wells, stop incubation if necessary, responsive to determining that a level of growth in the control wells meets or exceeds a threshold level of growth, perform an automated antimicrobial susceptibility test assays for one or more carbapenems and/or beta-lactam/beta-lactamase inhibitors on incubated samples in the test panel, perform one or more endpoint assays on incubated samples in the test panel, measure an optical output from the sample in the plurality of wells of the test panel, the optical output corresponding to an amount of the microorganism remaining in each of the plurality of wells; and report at least one of: a minimum inhibitory concentration of and/or a qualitative susceptibility interpretation for the microorganism remaining in each of the plurality of wells and the plurality of antimicrobials, such that the results of the carbapenemase and/or beta-lactamase assays influence algorithmic MIC determinations of one or more carbapenems and/or beta lactams.

In another embodiment, this disclosure describes a method for performing automated antimicrobial susceptibility testing of an antimicrobial. This method includes performing a dilution assay, comprising inoculating a microbial inoculum of concentration $C_0$ into a plurality of fluid wells defining a dilution series of an antimicrobial, and measuring in each of the plurality of fluid wells a signal associated with microbial growth (and optionally comparing the signal measured in each of the plurality of fluid wells and based on said comparison, defining a minimum inhibitory concentration (MIC) of the antimicrobial). In parallel, this method includes performing an assay for resistance to the antimicrobial, the assay comprising measuring a signal associated with resistance to the antimicrobial in a first well comprising an antimicrobial and a microbial inoculum with concentration $C_R$, measuring a signal associated with resistance in a second well, comprising different contents than the first well and thereby acting as a control for the first well, and combining the data derived from the dilution assay with that derived from the carbapenemase assay to define a minimum inhibitory concentration (MIC) of the carbapenem antimicrobial and label the microorganism as carbapenem susceptible or carbapenem resistant (and optionally comparing the signals measured from the first and second wells and based on the comparison, labeling the microbial inoculum as susceptible or resistant to the antimicrobial).

In yet another embodiment, the signal associated with resistance to the antimicrobial is a signal associated with enzyme catalyzed degradation of the antimicrobial.

In yet another embodiment, the second well of the resistance assay either a) comprises an inhibitor of a resistance factor or b) does not comprise the microbial inoculum. Further, the resistance assay may comprise a third well and optional fourth well that serve as controls for monitoring the enzymatic degradation reaction. In yet another embodiment, $C_R>C_0$. Alternatively, $C_R \geq 10 \times C_0$. Alternatively, two or more different resistance assays are performed in parallel for a single sample with inoculation at concentrations $C_{R1}$ and $C_{R2}$. In yet another embodiment, $C_{R1}=C_{R2}$. Alternatively, $C_{R1} \neq C_{R2}$.

In another aspect of this disclosure, a method for performing automated antimicrobial susceptibility testing of a carbapenem antimicrobial is described. This method includes performing a dilution assay, comprising inoculating a microbial inoculum of concentration $C_0$ into a plurality of fluid wells defining a dilution series of a carbapenem antimicrobial, and measuring in each of the plurality of fluid wells a signal associated with microbial growth (and optionally comparing the signal measured in each of the plurality of fluid wells and based on said comparison, defining a minimum inhibitory concentration (MIC) of the carbapenem antimicrobial). This method further comprises in parallel with the dilution assay, performing a carbapenemase assay comprising measuring a signal associated with carbapenem degradation in a first well comprising a carbapenem antimicrobial and a microbial inoculum with concentration $C_R$, and optionally ionic zinc, measuring a signal associated with carbapenem degradation in one or more additional wells, comprising different contents than the first well and thereby acting as controls for the first well, and comparing the signals measured from the carbapenemase assay wells and combining the data derived from the dilution assay with that derived from the carbapenemase assay to define and label the microorganism as carbapenem susceptible or carbapenem resistant.

In yet another embodiment, $C_R>C_0$.

In yet another embodiment, the method further comprises the step of reporting to a user the result of the carbapenemase assay.

In yet another embodiment, carbapenem degradation is determined by a signal associated with an indicator. In this method, the indicator may be a fluorescent or optical pH indicator.

In yet another embodiment, antimicrobial $C_R>10\times C_0$.

In yet another embodiment, $C_R<1\times 10^8$ CFU intact microbes.

In another embodiment, the pH indicator is one or more of fluorescein, pyranine, tinopal, or a derivative thereof.

In another embodiment, the ionic zinc is selected from one or more of zinc sulfate, zinc chloride, zinc hydroxide.

In yet another embodiment, the results of the carbapenemase assay are input to the algorithm that determines carbapenem MICs and are reported to the user.

In yet another embodiment, the carbapenem is selected from imipenem and biapenem and their derivatives.

In another embodiment, the assay wells are optically interrogated after less than or equal to 3, 6, 8, 10 hours of incubation under conditions that promote microbial growth.

In another embodiment, three wells are utilized for carbapenemase control assays. Further, the first control well may comprise the microbial inoculum at $C_R$ and a pH indicator and ionic zinc. Even further, the second control well may comprise a pH indicator and ionic zinc and does not include the carbapenem and optionally the microbial inoculum at $C_0$. Also, the third well may comprise the carbapenem, a pH indicator, and ionic zinc.

In another embodiment, one or more additional wells comprise beta-lactamase inhibitors.

BRIEF DESCRIPTION OF THE DRAWINGS

FIG. 1 depicts exemplary data from beta-lactamase inhibitor assay tests of clavulanic acid and tazobactam with three microbial strains.

DETAILED DESCRIPTION

Overview

Generally, this disclosure focuses on beta lactamase and/or carbapenemase assays that are performed in parallel with standard phenotypic AST assays on an automated analyzer, e.g., as described in U.S. Pat. No. 10,161,948 to Vacic et al, which is incorporated by reference herein for all purposes. In several exemplary embodiments described herein, both types of assays are run on the same cartridge such that only a single cartridge is required for all tests for the automated analyzer.

Those of skill in the art will appreciate that the integration of these two assays into a single automated process involves several departures from existing industry standard processes. First, commercially available AST systems generally require all wells of the multi-well AST testing vessel (e.g., microtiter plate, multi-well cassette, etc.) be loaded with substantially equivalent quantities of microbial sample, so as to ensure that differences in growth observed across antimicrobial dilution series are not due to differences in initial loading of the wells. By contrast, in some of the embodiments of this disclosure, the time-to-result for carbapenemase and beta-lactamase assays is reduced by increasing the quantity of microorganisms in the reservoirs for these tests relative to the lower microorganism concentration present in the plurality of wells in the panel that are used for MIC determinations, as is discussed in greater detail below.

Second, existing automated AST systems generally take one of two approaches to carbapenemase or beta-lactamase testing: first, in an automated sample in which beta lactam or carbapenem resistance is suspected based upon algorithmic interpretations of growth curve results, the incubation period will be continued until the algorithmic interpretation of the growth curves is confident the resistance either is or is not present. This may add significant time before AST results are available due to the inducible nature of some resistance mechanisms, as known to those skilled in the art. This growth curve-based approach has the advantage of automation, but it can extend the time-to-result by hours, and in laboratories staffed in discontinuous shifts (e.g., without an overnight shift), extended assay times may shift the result from the same day to the following morning. In a second approach, a carbapenemase or beta lactamase assay is performed offline, independently of the automated AST assay. This approach may allow a result to be obtained and reported sooner, but it may also be more resource intensive than a fully automated process, and the separation of the AST and resistance assays raises a risk that data from both assays will not be associated with the same patient record during the period where the AST results are interpreted and prescribing decisions are made. The systems and methods presented herein leverage the advantages of both approaches yet can reduce or eliminate delays in delivery of results and integrate data from both assays into a single output. In the preferred embodiment, the results from the carbapenemase and/or beta-lactamase assays are used to influence the algorithmic MIC determinations of results from the appropriate carbapenem and beta lactam dilution series. In additional embodiments, the results from the carbapenemase and/or beta-lactamase assays may be provided to the user.

In some embodiments of this disclosure, beta-lactamase or carbapenemase activity is measured indirectly, for example by detecting a change in pH caused by the liberation of free acids by degradation of the antimicrobial. Those of skill in the art will appreciate that pH in particular may be affected by factors other than enzyme-catalyzed degradation due to microbial resistance. The potential for these other factors to confound the results of AST and carbapenemase/beta-lactamase probe-based assays can be reduced by the inclusion of one or more carbapenemase or beta-lactamase inhibitors. By comparing the signal from an "inhibited" well to one containing the probe and microbes alone, the efficacy of the inhibitor may be tested. For example, tazobactam's inhibitory effects on a clinical *Escherichia coli* sample may be determined by setting up two wells containing *E. coli* and nitrocefin and adding tazobactam to the second well. By extending the dilution series, minimum inhibition concentrations may be obtained.

In some embodiments, such tests would be performed by an automated AST analyzer, in parallel with AST tests, and the combined results would add increased accuracy to the tests. Since some beta-lactamases may be induced by the presence of beta-lactams, it may be advantageous to perform beta-lactamase inhibitory testing after microbial growth in the presence a beta-lactam. In the case where the presence of the beta-lactam inhibits microbial growth, no useful data from beta-lactamase inhibitory testing may be obtained.

Any beta-lactamase probe may be utilized for these assays. Engineered probes with less-broad activity may also be used. However, the key to the assay concept is that the probe is sufficiently broad to ensure a plurality of potential beta-lactamase variants that can be inhibited by the inhibitor will degrade the probe for which the assay results will influence the MIC-determining algorithm of the AST platform.

By combining inhibitors in a single test well, information about the presence of beta-lactamase classes may be obtained. In this case, inhibitors may include drugs and potential drugs as well as agents with unacceptable toxicities for human use, such as EDTA, which is well-known to inhibit metallo-beta-lactamases (MBLs) but is toxic. An assay for carbapenemase activity may be developed by including inhibitors of non-carbapenemase ESBLs in one well, together with the clinical sample and nitrocefin, and comparing this to a sample comprising the clinical sample and nitrocefin without the inhibitors. Such inhibitors include, but are not limited to, clavulanate, cloxacillin, and tazobactam. Additional accuracy may be obtained by adding a third well comprising known inhibitors of carbapenems, including but not limited to avibactam, vaborbactam, and EDTA.

Information on carbapenemase presence may also be obtained by utilizing a carbapenem antimicrobial as a competitor to a beta-lactamase probe. In this case, one or more inhibitors may be added to inhibit non-carbapenemase beta-lactamase activity in all assay wells, in addition to a clinical microbe sample and a broad-spectrum probe, such as nitrocefin. Note a more narrow-spectrum probe may be advantageous here.

One well would then comprise a high concentration of a carbapenem, which would not be present in the second well. By comparing the rate of nitrocefin degradation in each well, the presence of a carbapenemase may be inferred: if the carbapenem retards the generation of the signal resulting from nitrocefin degradation, a carbapenemase is likely present. In alternative embodiments, oxacillin may be used in one or more additional wells as a competitor, specifically for the detection of "OXA" carbapenemases.

Exemplary carbapenemase assays may also utilize the acidimetric technique. Currently disclosed acidimetric carbapenemase assays utilize >$10^9$ CFU/mL microbes, complicating their use in automated AST testing following standard laboratory workflows, where <$5 \times 10^7$ CFU/mL microbes are commonly available. Furthermore, standard laboratory workflows for AST testing utilize intact microbes of which a plurality are viable. These standard workflow requirements challenge previously-disclosed carbapenemase assays, which rely on greater microbial quantities and lysed microbes. These requirements are due to the fact that many carbapenemases may be intracellular and may be expressed in low concentration at early timepoints due to their inducible nature.

Here we demonstrate the surprising finding that acidimetric carbapenemase assays may be performed using less than one-tenth ($\frac{1}{10}^{th}$) of the number of intact microbes by utilizing four assay wells to provide an appropriately normalized result. Additionally, the assay utilizes a fluorometric, rather than a colorimetric, pH probe, increases assay incubation times to 4 hours, and increases carbapenem concentrations to >1 mg/mL.

Here we further demonstrate the counter-intuitive finding that faster AST results may be made available by utilizing different microorganism concentrations in different test reservoirs of an automated AST panel. This is particularly surprising because existing automated AST platforms, including the Vitek2® (bioMérieux), MicroScan™ (Danaher/Beckman-Coulter), Phoenix® (Becton-Dickinson), and SensiTitire™ (ThermoFisher) provide dedicated hardware specifically to ensure all reservoirs on the panel inoculated with microorganisms (e.g. all reservoirs except the contamination control that is inoculated with zero microorganisms) receive a substantially equivalent quantity of microorganisms. This is the case because MICs are relative measurements, in which the growth in each reservoir of a dilution series of an antimicrobial is compared with the growth in other reservoirs of the same dilution series (and may be compared with that for other antimicrobials).

In contrast, here we demonstrate that AST result accuracy may be enhanced through the inoculation of two or more different quantities of microorganisms in different automated AST panel reservoirs. In particular, microorganisms inoculated into reservoirs comprising dilution series of antimicrobials may be of a substantially equivalent concentration, $C_0$, and microorganisms inoculated into specific resistance mechanism-determining assays may be of a different concentration, $C_R$. In particular, the concentrations may be such that $C_R=\alpha C_0$, where $\alpha$ is preferably greater than 1 and most preferably greater than 10.

In an exemplary embodiment, the assay comprises a minimum of 4 wells and utilizes a sample comprising intact microbes. The first well ($Well_1$) comprises a medium such as a buffered saline solution or a nutrient broth, a carbapenem, ionic zinc, and a pH indicator. The second well ($Well_2$) comprises the medium, a carbapenem, ionic zinc, a pH indicator, and a microbe sample comprising <1×10$^8$ CFU microbes. The third well ($Well_3$) comprises the medium, ionic zinc, and a pH indicator. The fourth well ($Well_4$) comprises the medium, ionic zinc, a pH indicator, and a microbe sample comprising <1×10$^8$ CFU microbes. The following formula can then be utilized to normalize the result:

Normalized Activity=($Well_1$−$Well_2$)−($Well_3$−$Well_4$)   [Formula 1]

The above says that imipenem degradation is the change in pH (e.g. loss of signal) due to the presence of microbes less the change in pH (e.g. loss of signal) due to microbes in solution only.

In additional embodiments, acidimetric methods may be utilized for testing inhibitors. For example, the addition of an inhibitor with known carbapenemase activity, such as avibactam or vaborbactam, to an additional well of the carbapenemase assay described above may serve as an assay for inhibitor activity. Typically, high sensitivity assays that are based on amplification (e.g., catalytic) can be performed only once since chemistries necessary for those assays usually destroy the target microorganism. Thus, the systems and methods described herein typically use two types of assays to address this issue. In some cases, a preliminary (e.g., checkpoint) assay can be performed first and can be repeated periodically to interrogate growth of uninhibited microorganisms (i.e., without antimicrobial presence). These checkpoint assays can be performed in wells referred to herein as control wells. Examples of typical control wells are a growth well containing microorganisms in nutrient broth and a contamination control well containing nutrient broth only. The system interrogates growth/no growth optically (e.g., absorbance, fluorescence metabolic dye, etc.) and once a particular ratio and/or kinetic change between the control wells is achieved and detected, one or more end point assays (e.g., an amplification assay or growth assay) can be initiated on samples disposed in other portions of the test panel (e.g., the rest of, or the entire, test panel). The samples, for example, can include microorganisms originating from a clinical sample. Additional wells, such as wells containing microorganisms in saline or other media that does not promote growth of microorganisms (i.e., due to lack of nutrients) can be utilized for growth check and MIC determination. These wells can contain concentrations of microorganisms that are similar to the starting sample and referred to as "frozen in time" (e.g., FIT) control.

In some cases, the systems and methods described herein can be implemented to provide faster testing than some conventional systems. For example, though some automated systems may speed time to obtain results, the time-to-results for carbapenemase-expressing strains rarely meet the ~6-hour definition of "same-shift" results for many clinical laboratories. Because of this slow time-to-results and because AST results are complex and may utilize expert interpretation for clinical action, such conventional systems can result in a day delay between the onset of susceptibility testing and clinical action for patients infected with these difficult-to-treat samples.

TABLE 1

Carbapenemase assay results for 26 microbial strains within 4 hours.

| Species | Strain | Known Carbapenemase | Other known resistance | Carbapenemase Activity |
|---|---|---|---|---|
| E. coli | CDC CNP 73 | KPC | | 3480.1845 |
| E. coli | CDC CRE 26 | NDM | | 41326.61 |
| E. coli | CDC CRE 03 | KPC-3 | | 7149.729 |
| E. coli | CDC CRE 07 | NDM | | 27447.359 |
| E. coli | CDC BIT 01 | KPC | | 8803.9255 |
| E. coli | CDC CNP 38 | NDM | | 19534.8825 |
| E. coli | CDC CRE 17 | NDM | | 36400.9235 |
| E. coli | CDC CNP 27 | none | ESBL+ | −2401.2335 |
| E. coli | CDC CNP 54 | none | Amp beta lactamase | −1950.443 |
| E. coli | SML 19 | none | | −2540.0545 |
| E. coli | SML20 | none | | −2734.3825 |
| E. coli | AR0346 | none | ESBL+ | −2560.861 |
| E. coli | AR0348 | none | | −2960.1665 |
| E. coli | AR0349 | none | ESBL+ | −2861.008 |
| E. coli | AEL18 | none | | −1551.4885 |
| E. coli | AEL19 | none | | −696.4825 |
| E. coli | AEL 20 | none | | −882.3165 |
| E. coli | TRICORE 71 | none | | −1138.2225 |
| E. coli | TRICORE 72 | none | | −2554.797 |
| E. coli | 25922 | none | | −2106.4115 |
| K. pneumoniae | CDC CNP 03 | IMP | | 3662.106 |
| K. pneumoniae | CDC CNP 08 | OXA-181 | | 1323.2385 |
| K. pneumoniae | CDC CNP 09 | VIM | | 2315.76 |
| K. pneumoniae | 700603 | none | | −2659.8725 |
| K. pneumoniae | SML86 | none | | −1861.1485 |
| K. pneumoniae | SML87 | none | | −3075.4205 |

TABLE 2

Carbapenemase assay results for various concentrations of imipenem within 4 hours.

| Species | Strain | Known Carbapenemase | Carbapenemase Activity in various concentrations of imipenem | | | | | |
|---|---|---|---|---|---|---|---|---|
| | | | 50 µg/mL | 125 µg/mL | 250 µg/mL | 500 µg/mL | 1250 µg/mL | 2500 µg/mL |
| E coli | ATCC 25922 | none | −70.5 | −522 | −599.5 | −558.5 | −463.5 | −282 |
| K pneumoniae | ATCC BAA-2342 | KPC | 1817 | 4702.5 | 4270.5 | 3708 | 3251 | 3114.5 |
| E coli | AR 114 | KPC3 | 930.5 | 3793.5 | 3342.5 | 2784.5 | 2173.5 | 1825.5 |
| E coli | AR 69 | NDM | 1111 | 3367 | 2827 | 2300.5 | 1908.5 | 1902.5 |
| K pneumoniae | AR 34 | IMP | 1034.5 | 2776.5 | 2456.5 | 1807.5 | 1148 | 637.5 |

TABLE 3

Carbapenemase assay performed with dried reagents.

| Species | Strain | Known Carbapenemase | Carbapenemase Activity |
|---|---|---|---|
| E coli | ATCC 25922 | none | −6116 |
| K pneumoniae | ATCC BAA-1705 | KPC2 | 19742 |
| K pneumoniae | ATCC BAA-2814 | KPC3 | 18057 |
| K pneumoniae | ATCC 700603 | none | −2026 |

EXAMPLES

Example 1

Microbes were prepared by diluting colonies into saline to reach a McFarland value of 0.5, which was verified using a spectrophotometer. This was diluted 1:20 into saline and 50 µl of inoculum was added to wells of a 384-well plate. For each strain, 25 µl of solutions containing either 0.25 mg/mL nitrocefin alone (Nitro), 0.25 mg/mL nitrocefin and 4 µg/mL clauvulanate (Nitro Clav), or 0.25 mg/mL nitrocefin and 4 µg/mL tazobactam (Nitro Tazo) were added to duplicate wells. Inoculated plates were incubated at 35° C., shaking at 150 rpm for 4 hours. Absorbance was read at 490 nm and values shown in FIG. 1 are the absorbance in the indicated condition minus the absorbance from microbial inoculum alone without nitrocefin. A greater value indicates microbial ability to degrade nitrocefin, and thus, the presence of a beta lactamase. A reduction in absorbance value in the presence of an inhibitor indicates the beta lactamase present is sensitive to the inhibitor. For the data presented here, EC 25922 does not contain a beta lactamase, but the other two organisms do. Further, the inhibitors are both active against each of the strains with known beta lactamases.

Example 2

Microbes were prepared by diluting colonies into saline to reach a McFarland value of 0.5, which was verified using a spectrophotometer. 100 µL of the microbe solution was added to each of 2 wells in a 96-well plate. 100 µL of saline was added to 2 separate wells on the plate. 100 µL of an imipenem solution containing 5 mg/mL imipenem, 0.1 mM $ZnSO_4$, and 10 µM Fluorescein Na salt, pH 8, was added to one of the microbe-containing wells ($Well_2$) and one of the saline wells ($Well_1$). 100 µL of a negative control solution containing 0.1 mM $ZnSO_4$, and 10 µM Fluorescein Na salt pH 7.5, was added to one of the microbe-containing wells ($Well_4$) and one of the saline wells ($Well_3$). Plates were incubated, shaking at 35° C. for 4 hours and fluorescence of the wells was read at Em=490 nm/Ex=510 nm. The values reported were calculated to determine the hydrolysis of imipenem by the microbes using Equation 1. These data are tabulated in Table 1.

Example 3

Microbes were prepared by diluting colonies into saline to reach a McFarland value of 0.5, which was verified using a spectrophotometer. 25 µL of the microbe solution was added to each of 2 wells in a 384-well plate. 25 µL of saline was added to 2 separate wells on the plate. 25 µL of an imipenem solution containing imipenem, 0.1 mM $ZnSO_4$, and 10 µm Fluorescein Na Salt, pH 8, was added to one of the microbe-containing wells ($Well_2$) and one of the saline wells ($Well_1$). 25 µM of a negative control solution containing 0.1 mM $ZnSO_4$, and 10 µM Fluorescein Na Salt, pH 7.5, was added to one of the microbe containing wells ($Well_4$) and one of the saline wells ($Well_3$). Plates were incubated, shaking at 35° C. for 3 hours and fluorescence of the wells was read at Em=490/Ex=510. This organization of the assay was performed multiple times, varying the concentration of imipenem in solution. The assay was run with final imipenem concentrations of 50 µg/mL, 125 µg/mL, 250 µg/mL, 500 µg/mL, 1250 µg/mL, and 2500 µg/mL. The values reported were calculated to determine the hydrolysis of imipenem by the microbes using Equation 1. These data are tabulated in Table 2.

Example 4

Microbes were prepared by diluting colonies into saline to reach a McFarland value of 0.5, which was verified using a spectrophotometer. 100 µL of the microbe solution was added to each of 2 wells in a vacuum-dried 96-well plate ($Well_2$, $Well_4$). 100 µL of saline was added to 2 separate wells on the plate ($Well_1$ and $Well_3$). Following addition of microbial or saline solutions, the final concentrations of the contents in each well were: 300 µg/mL imipenem, 0.05 mM $ZnSO_4$, and 10 µM Fluorescein Na Salt, pH 7.8, ($Well_1$, $Well_2$); only 0.05 mM $ZnSO_4$ and 10 µM Fluorescein Na Salt, pH 7.8, were present in the third and four wells ($Well_3$, $Well_4$). Plates were incubated, shaking at 35° C. for 4 hours and fluorescence of the wells was read at Em=490/Ex=510. The values reported were calculated to determine the hydrolysis of imipenem by the microbes using Equation 1. These data are tabulated in Table 3.

The invention claimed is:

1. An automated antimicrobial susceptibility test assay for one or more carbapenems and/or beta-lactam/beta-lactamase inhibitors, which assay comprises a single cartridge for the same microbial inoculum comprising:
   a. two or more assay wells comprising an antimicrobial dilution series for the specific carbapenem antimicrobial;

b. a series of assay wells for a carbapenemase assay different from the antimicrobial dilution series comprising:
   i. one or more assay wells comprising saline, a carbapenem, ionic zinc, and a pH indictor, wherein the one or more assay wells do not receive a microbial inoculum;
   ii. one or more assay wells comprising saline, a carbapenem, ionic zinc, a pH indictor, for inoculation with a microbe sample comprising $<1\times10^8$ CFU intact microbes;
   iii. one or more assay wells comprising saline, ionic zinc, and a pH indictor, wherein the one or more assay wells do not receive a microbial inoculum;
   iv. one or more assay wells comprising saline, ionic zinc, a pH indictor, for inoculation with a microbe sample comprising $<1\times10^8$ CFU intact microbes.

2. The assay of claim 1, wherein the carbapenem is selected from imipenem or biapenem.

3. The assay of claim 1, wherein the pH indicator is fluorescein.

4. The assay of claim 1, wherein the ionic zinc is selected from zinc sulfate, zinc chloride.

5. The assay of claim 1, wherein the assay wells are optically interrogated after less than or equal to 3, 6, 8 or 10 hours of incubation under conditions that promote microbial growth.

6. The assay of claim 1, wherein one or more additional wells comprise beta lactamase inhibitors.

7. A method for performing automated antimicrobial susceptibility testing of an antimicrobial comprising:
   performing a dilution assay, comprising:
      inoculating a microbial inoculum of concentration $C_0$ into a plurality of fluid wells defining a dilution series of an antimicrobial;
      measuring in each of the plurality of fluid wells a signal associated with microbial growth; and
   in parallel with the dilution assay, performing an assay for inducible resistance to the antimicrobial, the assay comprising:
      measuring a signal associated with resistance to the antimicrobial in a first well comprising an antimicrobial and a microbial inoculum with concentration $C_R$, wherein $C_R \neq C_0$;
      measuring a signal associated with induced resistance in a second well, comprising different contents than the first well and thereby acting as a control for the first well; and
      combining the data derived from the dilution assay with that derived from the assay to define a minimum inhibitory concentration (MIC) of the antimicrobial and label the microorganism as antimicrobial susceptible or antimicrobial resistant.

8. The method of claim 7, further comprising comparing the signal measured in each of the plurality of fluid wells and based on said comparison, defining a minimum inhibitory concentration (MIC) of the antimicrobial.

9. The method of claim 7, wherein the signal associated with induced resistance to the antimicrobial is a signal associated with enzyme catalyzed degradation of the antimicrobial.

10. The method of claim 7, wherein the second well of the inducible resistance assay either a) comprises an inhibitor of a resistance factor or b) does not comprise the microbial inoculum.

11. The method of claim 9, wherein the inducible resistance assay comprises a third well and optional fourth well that serve as controls for monitoring the enzymatic degradation reaction.

12. The method of claim 7, wherein $C_R > C_0$.

13. The method of claim 7, wherein $C_R \geq 10 \times C_0$.

14. The method of claim 7, wherein two or more different resistance assays are performed in parallel for a single sample with inoculation at concentrations $C_{R1}$ and $C_{R2}$.

15. The method of claim 14, wherein $C_{R1} = C_{R2}$.

16. The method of claim 14, wherein $C_{R1} \neq C_{R2}$.

17. An automated antimicrobial susceptibility testing system comprising:
   (a) an AST platform; and
   (b) an assay cartridge for use in said platform to perform a dilution assay, comprising:
      a plurality of fluid wells for inoculation with a microbial inoculum of concentration $C_0$, further comprising a dilution series of an antimicrobial;
      measuring in each of the plurality of fluid wells a signal associated with microbial growth; and
   an inducible resistance assay different from the dilution assay, comprising:
      a first well comprising the antimicrobial and a microbial inoculum with concentration $C_R$, wherein $C_R \geq 10 C_0$ and wherein a signal associated with resistance to the antimicrobial is measured;
      a second well, comprising different contents than the first well and thereby acting as a control for the first well, wherein a signal associated with induced resistance is measured;
   wherein the AST platform reports a minimum inhibitory concentration (MIC) of the antimicrobial determined by combining the data derived from the dilution assay with that derived from the inducible resistance assay to thereby identify the microorganism as antimicrobial susceptible or antimicrobial resistant.

18. The system of claim 17, wherein the minimum inhibitory concentration (MIC) of the antimicrobial is based on a comparison of the signal measured in each of the plurality of fluid wells.

19. The system of claim 17, wherein the signal associated with induced resistance to the antimicrobial is a signal associated with enzyme catalyzed degradation of the antimicrobial.

20. The system of claim 17, wherein the second well of the resistance assay either a) comprises an inhibitor of a resistance factor or b) does not comprise the microbial inoculum.

21. The system of claim 17, wherein the resistance assay comprises a third well and optional fourth well that serve as controls for monitoring the enzymatic degradation reaction.

22. The system of claim 17, wherein two or more different resistance assays are performed in parallel for a single sample with inoculation at concentrations $C_{R1}$ and $C_{R2}$.

23. The system of claim 17, wherein $C_{R1} = C_{R2}$.

24. The system of claim 17, wherein $C_{R1} \neq C_{R2}$.

* * * * *